United States Patent
Lutz

(10) Patent No.: US 12,029,773 B2
(45) Date of Patent: Jul. 9, 2024

(54) MASTIC-DERIVED NATURAL PROTECTANTS

(71) Applicant: Lincoln Manufacturing Inc., Lincoln, RI (US)

(72) Inventor: Patrick J. Lutz, Nazareth, PA (US)

(73) Assignee: BARENTZ NORTH AMERICA, LLC, Avon, OH (US)

( * ) Notice: Subject to any disclaimer, the term of this patent is extended or adjusted under 35 U.S.C. 154(b) by 0 days.

(21) Appl. No.: 16/404,478

(22) Filed: May 6, 2019

(65) Prior Publication Data

US 2019/0343911 A1 Nov. 14, 2019

Related U.S. Application Data

(60) Provisional application No. 62/671,269, filed on May 14, 2018.

(51) Int. Cl.
| | | |
|---|---|---|
| A61K 9/00 | (2006.01) | |
| A61K 36/77 | (2006.01) | |
| A61P 31/04 | (2006.01) | |
| A61Q 5/02 | (2006.01) | |
| A61Q 19/00 | (2006.01) | |

(52) U.S. Cl.
CPC ............ *A61K 36/77* (2013.01); *A61K 9/0014* (2013.01); *A61P 31/04* (2018.01); *A61Q 5/02* (2013.01); *A61Q 19/00* (2013.01)

(58) Field of Classification Search
CPC ...... A61K 36/77; A61K 9/0014; A61L 17/005
See application file for complete search history.

(56) References Cited

U.S. PATENT DOCUMENTS

| | | | | |
|---|---|---|---|---|
| 8,129,419 B2* | 3/2012 | Levy | ......................... | A61P 1/00 |
| | | | | 514/372 |
| 2004/0037790 A1* | 2/2004 | Watanabe | ............... | A61K 8/922 |
| | | | | 424/58 |
| 2011/0028525 A1* | 2/2011 | Diehl | ..................... | A01N 43/80 |
| | | | | 514/372 |
| 2012/0156351 A1* | 6/2012 | Miyazawa | ............... | A23L 27/88 |
| | | | | 426/538 |
| 2014/0234448 A1* | 8/2014 | Steve | ...................... | A01N 65/28 |
| | | | | 424/742 |

FOREIGN PATENT DOCUMENTS

| | | |
|---|---|---|
| EP | 2016827 A2 | 1/2009 |
| WO | WO-03092712 A1 | 11/2003 |
| WO | WO-2013006917 A1 | 1/2013 |

OTHER PUBLICATIONS

Fkour Sh et al (Effect of Pistacia antlantica Mastic Extract on Experimental Wound Healing and Various Biochemical Parameters of Blood Serum in Rabbit Models) (Year: 2017).*
Sotirios Paraschos et al (Chemical investigation and antimicrobial properties of mastic water and its major constituents; Food Chemistry 129, 2011 907-911) (Year: 2011).*
Of Kalinowska et al (Relationship between chemical structure and biological activity of alkali metal o-, m-and p-anisates. FT-IR and microbiological studies, Spectrochimica Acta Part A 82, 2011, 432-436) (Year: 2011).*
Kim et al (Combination of lauroyl aginate ethyl and nisin for biofouling control in reverse osmosis process, Destination 428, 2018, 12-20) (Year: 2018).*
Salawu et al (Antimicrobial activities of phenolic containing extracts of some tropical vegetables, African Journal of Pharmacy and Pharmacology vol. 5(4), 2011, 486-492) (Year: 2011).*
Paraschos et al (Chemical investigation and antimicrobial properties of mastic water and its major constituents, Food Chemistry 129 , 2011, 907-911) (Year: 2011).*
Kalinowska et al (Relationship between chemical structure and biological activity of alkali metalo-, m-and p-anisates. FT-IR and microbiological studies, Soectrochimica Acta Part A 82, 2011, 432-436) (Year: 2011).*
Reme et al (Efficacy of an ammonium lactate-piroctane olamine shampoo for the management of dry scaly seborrheic disorders in dogs, 20 ESVD-ECVD Congress, Sep. 8-10, 2005, Chalkidiki-Greece) (Year: 2005).*
Karar, et al., Identification, Characterization, Isolation and Activity Against Escherichiacoliog Quince (Cydonia Oblonga) Fruit Polyphenols, Food Research International, 2013, 65:121-129.
Paraschos, et al., Chios Gum Mastic: A Review of its Biological Activities, Current Medicinal Chemistry, 2012, 19:14:2292-2302.
Paraschos, et al., Chemical Investigation and Antimicrobial Properties of Mastic Water and Its Major Constituents, Food Chemistry, 2011, 129:3:907-911.
European Search Report issued in EP19174377 dated Jul. 2, 2019.

* cited by examiner

*Primary Examiner* — Micah Paul Young
(74) *Attorney, Agent, or Firm* — Blank Rome LLP

(57) ABSTRACT

The present invention relates to the use of natural protectants comprising a mastic extract and optionally a second component to prevent microbial growth and preserve a product. The invention also relates to the use of natural protectants comprising quinic acid or a salt thereof, ethyl lauroyl arginate or a salt thereof, and optionally a third component to prevent microbial growth and preserve a product.

16 Claims, No Drawings

MASTIC-DERIVED NATURAL PROTECTANTS

This application claims the benefit of U.S. Provisional Patent Application No. 62/671,269, filed May 14, 2018, which is hereby incorporated by reference.

FIELD OF THE INVENTION

The present invention relates to the use of natural protectants comprising a mastic extract and optionally a second component to prevent microbial growth and preserve a product. The invention also relates to the use of natural protectants comprising quinic acid or a salt thereof, ethyl lauroyl arginate or a salt thereof, and optionally a third component to prevent microbial growth and preserve a product.

BACKGROUND

There are many drawbacks to currently available natural and naturally-derived antimicrobial formulations. They are expensive, and high concentrations of them (for instance, >2%) are often required to prevent microbial growth and preserve a product. Many have undesirable colors and odors, have poor stability (for example, in aqueous systems), and are not effective against a broad spectrum of microorganisms. Additionally, some such natural or naturally-derived antimicrobial mixtures cause thinning of formulations. Many are oils or extracts which limits their usage in various formulations.

EP 2731634 discloses a disinfecting formulation comprises alcohol including ethanol; an essential oil comprising cineole, in particular eucalyptus oil; an emollient including glycerin; and other ingredients comprising piroctone olamine, acrylic acid based polymer and 2-amino-2-methyl-1-propanol.

There is a continuing need for low cost and safe natural preservative systems which are effective against a broad spectrum of microorganisms.

SUMMARY OF THE INVENTION

The natural protectants of the present invention are relatively cheap to make, easy to work with and incorporate into finished products, generally have no odor, and have reduced (compared to prior oil preservative systems) or no color. In one embodiment, the protectant comprises a mastic extract (such as mastic water) and optionally (i) one or more natural or naturally derived compounds and/or (ii) one or more other antimicrobials. One preferred embodiment is a protectant comprising mastic water and quinic acid or a salt thereof. Another preferred embodiment is a protectant comprising mastic oil and piroctone olamine. Yet another is a protectant comprising mastic water and ethyl lauroyl arginate (ELA) or a salt thereof (such as ethyl lauroyl arginate HCl). Yet another is a protectant comprising mastic water and p-anisic acid or a salt thereof (e.g., sodium p-anisate). Yet another is a protectant comprising mastic water and caprylhydroxamic acid or a salt thereof. Yet another is a protectant comprising mastic water, caprylhydroxamic acid or a salt thereof, and quinic acid or a salt thereof. Preferably, the protectant includes a synergistic amount of its components. For example, in one embodiment, the protectant comprises a synergistic amount of mastic water and quinic acid to inhibit microbial growth (e.g., fungi growth). Each of these embodiments may optionally include one or more additional natural or naturally derived compounds and/or one or more other antimicrobials.

Yet another embodiment is a protectant comprising quinic acid or a salt thereof, ethyl lauroyl arginate or a salt thereof (such as ethyl lauroyl arginate HCl), and optionally (i) one or more natural or naturally derived compounds and/or (ii) one or more other antimicrobials (such as one or more organic acids).

One embodiment is a product comprising an effective amount of a mastic extract to inhibit microbial growth (e.g., fungi growth) in the product, where the product is not intended for oral administration to an animal. The mastic extract, such as that described herein, is particularly effective as a protectant for personal care products.

Another embodiment is a method of killing and/or inhibiting the growth of microorganisms (e.g., fungi) on a substrate by applying an effective amount of a mastic extract to the substrate.

Yet another embodiment is a product comprising an effective amount (and preferably a synergistic amount) of (a) a mastic extract and (b) (i) one or more natural or naturally derived compounds and/or (ii) one or more other antimicrobials to inhibit microbial growth (e.g., fungi growth) in the product, where the product is not intended for oral administration to an animal. In one embodiment, the product comprises an effective amount (and preferably a synergistic amount) of mastic water and quinic acid. In another embodiment, the product comprises an effective amount (and preferably a synergistic amount) of mastic oil and piroctine olamine. In yet another embodiment, the product comprises an effective amount (and preferably a synergistic amount) of mastic water and ELA or a salt thereof (such as ELA HCl). In yet another embodiment, the product comprises an effective amount (and preferably a synergistic amount) of mastic water and p-anisic acid or a salt thereof (such as sodium p-anisate). In yet another embodiment, the product comprises an effective amount (and preferably a synergistic amount) of mastic water and caprylhydroxamic acid or a salt thereof. In yet another embodiment, the product comprises an effective amount (and preferably a synergistic amount) of mastic water, caprylhydroxamic acid or a salt thereof, and quinic acid or a salt thereof. The product can be, for instance, a personal care product, such as shampoo.

Yet another embodiment is a method of killing and/or inhibiting the growth of microorganisms (e.g., fungi) on a substrate comprising applying an effective amount (and preferably a synergistic amount) of (a) a mastic extract and (b) (i) one or more natural or naturally derived compounds and/or (ii) one or more other antimicrobials to the substrate. In one embodiment, an effective amount (and preferably a synergistic amount) of mastic water and quinic acid is applied to the substrate. In another embodiment, an effective amount (and preferably a synergistic amount) of mastic oil and piroctine olamine is applied to the substrate. In yet another embodiment, an effective amount (and preferably a synergistic amount) of mastic water and ELA or a salt thereof (such as ELA HCl) is applied to the substrate. In yet another embodiment, an effective amount (and preferably a synergistic amount) of mastic water and p-anisic acid or a salt thereof (such as sodium p-anisate) is applied to the substrate. In yet another embodiment, an effective amount (and preferably a synergistic amount) of mastic water and caprylhydroxamic acid or a salt thereof is applied to the substrate. In yet another embodiment, an effective amount (and preferably a synergistic amount) of mastic water, caprylhydroxamic acid or a salt thereof, and quinic acid or a salt thereof is applied to the substrate.

Yet another embodiment is a method of killing and/or inhibiting the growth of microorganisms (e.g., fungi) on a substrate comprising applying an effective amount (and preferably a synergistic amount) of (a) quinic acid or a salt thereof, (b) ethyl lauroyl arginate or a salt thereof (such as ethyl lauroyl arginate HCl), and optionally (i) one or more natural or naturally derived compounds and/or (ii) one or more other antimicrobials (such as one or more organic acids) to the substrate.

Yet another embodiment is a concentrate comprising (or consisting essentially of, or consisting of) (a) a mastic extract and (b) (i) one or more natural or naturally derived compounds and/or (ii) one or more other antimicrobials for inhibiting microbial growth (e.g., fungi growth). In one embodiment, the concentrate comprises (or consists essentially of, or consists of) (a) mastic water, quinic acid, and optionally water, (b) mastic oil, piroctine olamine, and optionally water, (c) mastic water, ELA or a salt thereof (such as ELA HCl), and optionally water, (d) mastic water, p-anisic acid or a salt thereof (such as sodium p-anisate), and optionally water, (e) mastic water, caprylhydroxamic acid or a salt thereof, and optionally water, or (f) mastic water, caprylhydroxamic acid or a salt thereof, quinic acid, and optionally water.

Yet another embodiment is a concentrate comprising (or consisting essentially of, or consisting of) quinic acid or a salt thereof, ethyl lauroyl arginate or a salt thereof (such as ethyl lauroyl arginate HCl), and optionally (i) one or more natural or naturally derived compounds and/or (ii) one or more other antimicrobials (such as one or more organic acids).

DETAILED DESCRIPTION OF THE INVENTION

Definitions

As used herein, the term "about" represent an amount or condition near to the stated amount or condition that still performs a desired function or achieves a desired result. For example, the term "about" may refer to an amount or condition that deviates by no more than 10% (i.e., ±10%), by no more than 5%, by no more than 1%, by no more than 0.1%, or by no more than 0.01% from a stated amount or condition.

The term "microorganisms" includes, but is not limited to, bacteria, fungi, yeasts, algae, insects, and pests.

The term "personal care products" refers to products intended for application to the human body, such as to skin, hair, and nails, including, but not limited to, shampoos, conditioners, creams, lotions (such as body lotions), cosmetics, and soaps.

Mastic Extract

The product may contain an effective amount of mastic extract (such as mastic oil or mastic water) to inhibit microbial growth in the product.

A mastic extract is derived from a mastic tree (Pistacia lentiscus). Suitable mastic extracts include, but are not limited to, mastic oil, mastic water, and any combination of any of the foregoing.

Mastic oil can be obtained from mastic by, for example, steam distillation.

Mastic water can be obtained as a byproduct during the steam distillation of mastic, such as from the steam distillation of mastic resin (the resin of Pistacia lentiscus var. chia).

In one embodiment, the product contains from about 0.001 to about 10% by weight of mastic extract, such as from about 0.001 to about 4%, from about 0.01 to about 2%, from about 0.05 to about 2%, from about 0.1 to about 2%, or from about 0.1 to about 1% by weight of mastic extract, based upon 100% total weight of product. For example, the product may contain from about 0.1 to about 10% by weight of mastic oil, such as from about 0.2 to about 8% or from about 0.3 to about 5% mastic oil. The product may contain from about 0.1 to about 10% by weight of mastic water, such as from about 0.5 to about 8% or from about 1 to about 7% mastic water (e.g., from about 1 to about 2% by weight of mastic water).

Mastic Extract Combinations

The product may contain an effective amount of mastic extract and (i) one or more natural or naturally derived compounds and/or (ii) one or more other antimicrobials (such as one or more synthetic antimicrobials) to inhibit microbial growth in the product. In one embodiment, the product contains an effective amount of mastic extract and one or more natural or naturally derived compounds to inhibit microbial growth in the product.

Suitable natural or naturally derived compounds include, but are not limited to, quinic acid or a salt thereof, ethyl lauroyl arginate (ELA) or a salt thereof (including ethyl lauroyl arginate HCl), p-anisic acid or a salt thereof (e.g., sodium p-anisate), caprylhydroxamic acid or a salt thereof, 1,3 propanediol (only all natural type), glycereth-2 cocoate, benzyl alcohol (naturally derived from cassia), glycerin, organic solvents (e.g., ethylhexyl glycerin, phenoxyethanol, caprylyl glycols, pentylene glycol (natural), phenethyl alcohol (natural), and hexylene glycol), organic acids (e.g., sorbic acid, benzoic acid, and citric acid), and any combination of any of the foregoing.

In one preferred embodiment, the natural or naturally derived compound(s) are quinic acid, caprylhydroxamic acid, or any combination of any of the foregoing. In one embodiment, quinic acid is obtained from a plant source, such as cranberries.

In one preferred embodiment, the natural or naturally derived compound is quinic acid. In another preferred embodiment, the natural or naturally derived compound is ELA or a salt thereof, such as ethyl lauroyl arginate or ethyl lauroyl arginate HCl. In one embodiment, the natural or naturally derived compound is ethyl lauroyl arginate. In another embodiment, the natural or naturally derived compound is ethyl lauroyl arginate HCl.

In one embodiment, the weight ratio of (i) mastic extract (such as mastic water or mastic oil) to (ii) one or more natural or naturally derived compounds or other antimicrobials may range from about 0.01:100 to about 100:0.01, preferably ranges from about 0.1:20 to about 20:0.1, such as from about 1:10 to about 10:1. In one embodiment, the weight ratio of mastic water to quinic acid (or a salt thereof) ranges from about 1:5 to about 20:1, such as from about 10:1 to about 1:1, from about 8:1 to about 2:1, from about 6:1 to about 3:1, or about 4:1. In another embodiment, the weight ratio of mastic oil to piroctone olamine ranges from about 1:5 to about 20:1, such as from about 10:1 to about 1:1, from about 8:1 to about 2:1, from about 6:1 to about 3:1, or about 4:1. In yet another embodiment, the weight ratio of mastic water to ELA or a salt thereof (such as ELA HCl) ranges from about 1:10 to about 10:1, such as from about 5:1 to about 1:5, from about 3:1 to about 1:3, from about 2:1 to about 1:2, or about 1:1. In yet another embodiment, the weight ratio of mastic water to p-anisic acid or a salt thereof (such as sodium p-anisate) ranges from about 1:5 to about 20:1, such as from about 10:1 to about 1:1, from about 8:1 to about 2:1, from about 6:1 to about 3:1, or about 4:1.

In another embodiment, the product contains (i) from about 0.001 to about 10% by weight of mastic extract, such as from about 0.001 to about 4%, from about 0.01 to about 2%, from about 0.05 to about 2%, from about 0.1 to about 2%, or from about 0.1 to about 1% by weight of mastic extract, based upon 100% total weight of product, and (ii) from about 0.001 to about 10% by weight of natural and naturally derived compounds or other antimicrobials, such as from about 0.001 to about 4%, from about 0.01 to about 2%, from about 0.05 to about 2%, from about 0.1 to about 2%, or from about 0.1 to about 1% by weight of natural and naturally derived compounds or other antimicrobials, based upon 100% total weight of product.

In another embodiment, the product contains an effective amount of mastic extract and one or more other antimicrobials (such as one or more synthetic antimicrobials) to inhibit microbial growth in the product.

Suitable other antimicrobials (for example, synthetic antimicrobials) include, but are not limited to, pirotine olamine, and any combination of any of the foregoing.

In one embodiment, the weight ratio of (i) mastic extract (such as mastic water) to (ii) one or more other antimicrobials (for example, synthetic antimicrobials) may range from about 0.01:100 to about 100:0.01, preferably ranges from about 0.1:20 to about 20:0.1, such as from about 1:10 to about 10:1.

In another embodiment, the product contains (i) from about 0.001 to about 10% by weight of mastic extract, such as from about 0.001 to about 4%, from about 0.01 to about 2%, from about 0.05 to about 2%, from about 0.1 to about 2%, or from about 0.1 to about 1% by weight of mastic extract, based upon 100% total weight of product, and (ii) from about 0.001 to about 10% by weight of natural and naturally derived compounds or other antimicrobials, such as from about 0.001 to about 4%, from about 0.01 to about 2%, from about 0.05 to about 2%, from about 0.1 to about 2%, or from about 0.1 to about 1% by weight of natural and naturally derived compounds or other antimicrobials, based upon 100% total weight of product.

In another embodiment, the product contains (i) from about 0.001 to about 10% by weight of mastic oil, such as from about 0.001 to about 4%, from about 0.01 to about 2%, from about 0.05 to about 2%, from about 0.01 to about 1%, or from about 0.05 to about 0.5% by weight of mastic extract, based upon 100% total weight of product, and (ii) from about 0.001 to about 10% by weight of natural and naturally derived compounds or other antimicrobials, such as from about 0.001 to about 4%, from about 0.01 to about 2%, from about 0.05 to about 2%, from about 0.1 to about 2%, or from about 0.1 to about 1% by weight of natural and naturally derived compounds or other antimicrobials, based upon 100% total weight of product.

In one embodiment, the product contains mastic oil and piroctone olamine. The product may contain (i) from about 0.001 to about 10% by weight of mastic oil, such as from about 0.001 to about 4%, from about 0.01 to about 2%, from about 0.05 to about 2%, from about 0.01 to about 1%, or from about 0.05 to about 0.5% by weight of mastic oil, based upon 100% total weight of product, and (ii) from about 0.001 to about 10% by weight of piroctone olamine, such as from about 0.001 to about 4%, from about 0.01 to about 2%, from about 0.01 to about 1%, from about 0.01 to about 0.1%, or from about 0.02 to about 0.08% by weight of piroctone olamine, based upon 100% total weight of product.

In another embodiment, the product contains mastic water and ELA. The product may contain (i) from about 0.001 to about 10% by weight of mastic water, such as from about 0.1 to about 8%, from about 0.5 to about 5%, from about 1 to about 4%, from about 1 to about 3%, or from about 1.5 to about 2.5% by weight of mastic water, based upon 100% total weight of product, and (ii) from about 0.001 to about 10% by weight of ELA, such as from about 0.1 to about 8%, from about 0.5 to about 5%, from about 1 to about 4%, from about 1 to about 3%, or from about 1.5 to about 2.5% by weight of ELA, based upon 100% total weight of product.

In yet another embodiment, the product contains mastic water and p-anisic acid or a salt thereof (preferably sodium p-anisate). The product may contain (i) from about 0.001 to about 10% by weight of mastic water, such as from about 0.1 to about 8%, from about 0.5 to about 5%, from about 1 to about 4%, from about 1 to about 3%, or from about 1.5 to about 2.5% by weight of mastic water, based upon 100% total weight of product, and (ii) from about 0.001 to about 10% by weight of p-anisic acid or a salt thereof (preferably sodium p-anisate), such as from about 0.01 to about 8%, from about 0.1 to about 5%, from about 0.1 to about 1%, from about 0.2 to about 0.8%, or from about 0.3 to about 0.7% by weight of p-anisic acid or a salt thereof (preferably sodium p-anisate), based upon 100% total weight of product.

In yet another embodiment, the product contains mastic oil and p-anisic acid or a salt thereof (preferably sodium p-anisate). The product may contain (i) from about 0.001 to about 10% by weight of mastic oil, such as from about 0.1 to about 8%, from about 0.5 to about 5%, from about 1 to about 4%, from about 1 to about 3%, or from about 1.5 to about 2.5% by weight of mastic oil, based upon 100% total weight of product, and (ii) from about 0.001 to about 10% by weight of p-anisic acid or a salt thereof (preferably sodium p-anisate), such as from about 0.01 to about 8%, from about 0.1 to about 5%, from about 0.1 to about 1%, from about 0.2 to about 0.8%, or from about 0.3 to about 0.7% by weight of p-anisic acid or a salt thereof (preferably sodium p-anisate), based upon 100% total weight of product.

In yet another embodiment, the product contains mastic water and quinic acid. The product may contain (i) from about 0.001 to about 10% by weight of mastic water, such as from about 0.1 to about 8%, from about 0.5 to about 5%, from about 1 to about 4%, from about 1 to about 3%, or from about 1.5 to about 2.5% by weight of mastic water, based upon 100% total weight of product, and (ii) from about 0.001 to about 10% by weight of quinic acid, such as from about 0.1 to about 8%, from about 0.5 to about 5%, from about 1 to about 4%, from about 1 to about 3%, or from about 1.5 to about 2.5% by weight of quinic acid, based upon 100% total weight of product. Preferably, the weight ratio of mastic water to quinic acid ranges from about 10:1 to about 0.5:1 and is more preferably from about 6:1 to about 2:1 (for example, 3:1, 4:1, or 5:1). In one more preferred embodiment, the weight ratio of mastic water to quinic acid is about 4:1. One embodiment is a composition comprising mastic water and quinic acid where the composition is water-white (i.e., approaching water in colorlessness and clarity). Preferably, the composition is water soluble. The composition also preferably comprises a synergistic protective amount of mastic water and quinic acid (e.g., a synergistic protective amount against fungi).

Quinic Acid and ELA Combinations

The product may contain an effective amount of quinic acid or a salt thereof, ethyl lauroyl arginate or a salt thereof (such as ethyl lauroyl arginate HCl), and optionally (i) one or more natural or naturally derived compounds and/or (ii) one or more other antimicrobials (such as one or more organic acids).

Products

The products described above may be a solid or liquid. In a preferred embodiment, the products described herein (as well as the concentrates described herein) are substantially free or completely free of parabens (such as methylparaben, ethylparaben, and propylparaben), formaldehyde donors, and/or isothiazolinones. According to one embodiment, the product (or concentrate) contains less than about 2, 1.5, 1, 0.5, 0.4, 0.3, 0.25, 0.2, 0.15, 0.1, 0.09, 0.08, 0.07, 0.06, 0.05, 0.04, 0.03, 0.02, or 0.01% by weight of parabens, formaldehyde donors, and/or isothiazolinones, based upon 100% total weight of product (or concentrate). According to one embodiment, the product (or concentrate) does not contain a preservative effective amount of a preservative. According to yet another embodiment, the product (or concentrate) is all natural. According to yet another embodiment, the product contains less than a smelling or coloring effective amount of the mastic extract.

In another embodiment, the product is substantially free or completely free of artificial (or synthetic) preservatives. According to one embodiment, the product contains less than about 2, 1.5, 1, 0.5, 0.4, 0.3, 0.25, 0.2, 0.15, 0.1, 0.09, 0.08, 0.07, 0.06, 0.05, 0.04, 0.03, 0.02, or 0.01% by weight of synthetic preservatives, based upon 100% total weight of product.

In one embodiment, the product (for example, a shampoo) has a pH below about 8.

In one embodiment, the product is not intended for oral administration to an animal (e.g., a human subject). In another embodiment, the product is other than a foodstuff, pharmaceutical, cosmetic, or nutritional supplement. For example, the product can be a household (e.g., personal care), industrial, or institutional product. In one preferred embodiment, the product is a personal care product, such as a shampoo, body lotion, conditioner, or soap.

The mastic extract optionally in combination with one or more natural or naturally derived compounds and/or other antimicrobials may be incorporated into substrates susceptible to microbial growth as a protectant to inhibit microbial growth. Likewise, the combination of quinic acid or a salt thereof, ethyl lauroyl arginate or a salt thereof (such as ethyl lauroyl arginate HCl), and optionally (i) one or more natural or naturally derived compounds and/or (ii) one or more other antimicrobials (such as one or more organic acids) may be incorporated into substrates susceptible to microbial growth as a protectant to inhibit microbial growth. Suitable substrates include, but are not limited to, a personal care product, such as a shampoo, conditioner, cream, lotion (such as body lotion), cosmetic, or soap; a household product, such as a fabric softener, laundry detergent, or hard surface cleaner; or an industrial product, such as paint, coatings, wood, textile, adhesive, sealant, leather, rope, paper, pulp, paper board, sheet rock, ceiling tiles, plastic, fuel, petroleum, oil, rubber working fluid, metal working fluid, starches (such as pet food starch), or mineral slurry, such as a slurry of clay, calcium carbonate, or titanium oxide ($TiO_2$).

Generally, the mastic extract alone or in combination with the one or more natural or naturally derived compounds and/or other antimicrobials acts quickly (e.g., reduces the microorganism (e.g., bacteria and/or fungi) count by 95, 99, 99.9, or 99.99% typically within an hour) and maintains efficacy (e.g., maintains less than 1,000 or 100 cfu/g) over long periods of time (e.g., for at least 7, 10, 14, or 28 days). Likewise, the combination of quinic acid or a salt thereof, ethyl lauroyl arginate or a salt thereof (such as ethyl lauroyl arginate HCl), and optionally (i) one or more natural or naturally derived compounds and/or (ii) one or more other antimicrobials (such as one or more organic acids) acts quickly (e.g., reduces the microorganism (e.g., bacteria and/or fungi) count by 95, 99, 99.9, or 99.99% typically within an hour) and maintains efficacy (e.g., maintains less than 1,000 or 100 cfu/g) over long periods of time (e.g., for at least 7, 10, 14, or 28 days).

The protectant, such as that containing the mastic extract with or without the one or more natural or naturally derived compounds and/or other antimicrobials, may include a solvent, such as water and water miscible solvents, including, but not limited to, alcohols (e.g., methanol, ethanol, propanol, iso-propanol, and butanol), glycols (e.g. glycerin, diglycerin, butylene glycol, butoxydiglycol, propylene glycol, and dipropylene glycol), esters, ethers, polyethers, and any combination of any of the foregoing. For example, the solvent may comprise water and one or more glycol and/or one or more alcohol, such as glycerin, phenoxyethanol, benzyl alcohol, or ethanol. A specific solvent system comprises water and a glycol, such as glycerin. A second specific solvent system comprises water and an alcohol, such as ethanol.

The protectant may be incorporated into an aqueous or oil based system or an emulsion. A suitable solvent for an oil based system is phenoxyethanol and/or benzyl alcohol.

In one embodiment, the protectant is comprised of all natural products. The protectant can be a liquid or a solid (e.g., a powder).

To prepare a formulation containing the product of the present invention, a concentrate of the protectant may be first prepared. The conentrate may be prepared by mixing the individual components. The concentrate may include from about 0.01 to about 100% by weight of the protectant such as from about 5 to about 80% by weight of the protectant, based upon 100% total weight of concentrate. For a two-component protectant, the concentrate broadly contains from about 0.01 to about 99.99% by weight of the mastic extract and from about 99.99% to about 0.01% by weight of one or more natural or naturally derived compounds and/or other antimicrobials, based upon 100% total weight of concentrate.

One embodiment is a concentrate comprising from about 5 to about 50% by weight of quinic acid or a salt thereof and from about 50% to about 95% by weight of mastic water, based upon 100% total weight of the concentrate. In one preferred embodiment, the concentrate comprises from about 15 to about 30% by weight of quinic acid or a salt thereof and from about 70% to about 85% by weight of mastic water. In another preferred embodiment, the concentrate comprises from about 20 to about 25% by weight of quinic acid or a salt thereof and from about 80% to about 85% by weight of mastic water. A more preferred embodiment is a concentrate comprising about 20% quinic acid or a salt thereof and about 80% mastic water. In one embodiment, the concentrate is water-white (i.e., approaching water in colorlessness and clarity).

Another embodiment is a concentrate comprising from about 5 to about 50% by weight of piroctine olamine and from about 50% to about 95% by weight of mastic oil, based upon 100% total weight of the concentrate. In one preferred embodiment, the concentrate comprises from about 15 to about 30% by weight of piroctine olamine and from about 70% to about 85% by weight of mastic oil. In another preferred embodiment, the concentrate comprises from about 20 to about 25% by weight of piroctine olamine and from about 80% to about 85% by weight of mastic oil. A more preferred embodiment is a concentrate comprising about 20% piroctine olamine and about 80% mastic oil.

Yet another embodiment is a concentrate comprising from about 10 to about 90% by weight of ELA or a salt thereof (such as ELA HCl) and from about 90% to about 10% by weight of mastic water, based upon 100% total weight of the concentrate. In one preferred embodiment, the concentrate comprises from about 25 to about 75% by weight of ELA or a salt thereof (such as ELA HCl) and from about 75% to about 25% by weight of mastic water. In another preferred embodiment, the concentrate comprises from about 40 to about 60% by weight of ELA or a salt thereof (such as ELA HCl) and from about 60% to about 40% by weight of mastic water. A more preferred embodiment is a concentrate comprising about 50% ELA or a salt thereof (such as ELA HCl) and about 50% mastic water.

Yet another embodiment is a concentrate comprising from about 5 to about 50% by weight of p-anisic acid or a salt thereof (such as sodium p-anisate) and from about 50% to about 95% by weight of mastic water, based upon 100% total weight of the concentrate. In one preferred embodiment, the concentrate comprises from about 15 to about 30% by weight of p-anisic acid or a salt thereof (such as sodium p-anisate) and from about 70% to about 85% by weight of mastic water. In another preferred embodiment, the concentrate comprises from about 20 to about 25% by weight of p-anisic acid or a salt thereof (such as sodium p-anisate) and from about 80% to about 85% by weight of mastic water. A more preferred embodiment is a concentrate comprising about 20% p-anisic acid or a salt thereof (such as sodium p-anisate) and about 80% mastic water.

Yet another embodiment is a concentrate comprising from about 10 to about 90% by weight of caprylhydroxamic acid or a salt thereof and from about 90% to about 10% by weight of mastic water, based upon 100% total weight of the concentrate. In one preferred embodiment, the concentrate comprises from about 25 to about 75% by weight of caprylhydroxamic acid or a salt thereof and from about 75% to about 25% by weight of mastic water. In another preferred embodiment, the concentrate comprises from about 40 to about 60% by weight of caprylhydroxamic acid or a salt thereof and from about 60% to about 40% by weight of mastic water.

Yet another embodiment is a concentrate comprising from about 5 to about 50% by weight of caprylhydroxamic acid or a salt thereof, from about 5% to about 50% by weight of mastic water, and from about 5% to about 50% by weight of quinic acid or a salt thereof, based upon 100% total weight of the concentrate.

Yet another embodiment is a concentrate comprising from about 10 to about 90% by weight of ELA or a salt thereof (such as ELA HCl) and from about 90% to about 10% by weight of quinic acid or a salt thereof, based upon 100% total weight of the concentrate. In one preferred embodiment, the concentrate comprises from about 25 to about 75% by weight of ELA or a salt thereof (such as ELA HCl) and from about 75% to about 25% by weight of quinic acid or a salt thereof. In another preferred embodiment, the concentrate comprises from about 40 to about 60% by weight of ELA or a salt thereof (such as ELA HCl) and from about 60% to about 40% by weight of quinic acid or a salt thereof. A more preferred embodiment is a concentrate comprising about 50% ELA or a salt thereof (such as ELA HCl) and about 50% quinic acid or a salt thereof.

Before use, the concentrate may be diluted, such as with the same solvent as was used in the concentrate, and/or incorporated into a product. Use dilutions of the composition typically include an effective amount of protectant to inhibit microbial growth (e.g., fungi growth).

Generally, use dilutions contain from about 0.0001% or 0.01% to about 2% by weight of the concentrate. According to one preferred embodiment, use dilutions contain from about 0.1 to about 1% by weight of the concentrate. In more preferred embodiments, the use dilution contains 0.2, 0.25 or 0.30% by weight of the concentrate.

According to another embodiment, the protectant is incorporated into a product at a concentration of about 0.1 to about 1 or 2% by weight, based upon 100% total weight of product.

Method of Inhibiting Microbial Growth

Another embodiment of the present invention is a method for killing and/or inhibiting the growth of microorganisms, such as bacteria (e.g., *S. aureus* (ATCC #6538), *P. aeruginosa* (ATCC #9027), and *E. coli* (ATCC #8739)) and/or fungi (including plant and tree fungi) (e.g., *Candida albicans, Aspergillus niger* and *Phytophthora ramrum*), on a substrate by applying an effective amount of the protectant to the substrate or incorporating an effective amount of the protectant into the substrate. The protectant may be applied to or incorporated into the substrate by any method known in the art including, but not limited to, brushing, dipping, soaking, vacuum impregnation, and pressure treatment.

The protectant may be prepared by mixing the components and optionally, one or more solvents, and/or adjuvants. The mixture may be heated and/or stirred to expedite mixing.

EXAMPLE 1

The CTFA Preservative Challenge Test was performed on a shampoo containing the samples below against a mixture of fungi (*C. albicans* (ATCC# 10231) and *A. brasiliensis* (ATCC# 16404)) having an initial count of $7.9 \times 10^5$ cfu/mL or a mixture of bacteria having an initial count of $4 \times 10^6$ cfu/mL. The shampoos inoculated with bacteria were allowed to stand for 14 days and the shampoos inoculated with fungi were allowed to stand for 7 days. The samples were evaluated for surviving organisms on day 7 for fungi-innoculated shampoos and days 7 and 14 for bacteria-innoculated shampoos.

The results are shown in the table below.

| Sample | Mixed Fungi Day 7 Count (cfu/mL) | Mixed Bacteria Day 7 Count (cfu/mL) | Mixed Bacteria Day 14 Count (cfu/mL) |
|---|---|---|---|
| 0.5% Mastic oil | $6.9 \times 10^4$ (<90% kill reduction) | | |
| 0.1% Piroctine olamine | $5.9 \times 10^4$ (<90% kill reduction) | $1.2 \times 10^5$ (<97% kill reduction) | $1.3 \times 10^5$ (<97% kill reduction) |

-continued

| Sample | Mixed Fungi Day 7 Count (cfu/mL) | Mixed Bacteria Day 7 Count (cfu/mL) | Mixed Bacteria Day 14 Count (cfu/mL) |
|---|---|---|---|
| 0.2% Mastic oil and 0.05% piroctine olamine | 4.7 × 10$^2$ (>99.9% kill reduction) | | |
| 5% Mastic water | | 3.1 × 10$^4$ (<99% kill reduction) | |
| 5% ELA HCl | | | 1.3 × 10$^2$ (<99.9% kill reduction) |
| 2% Mastic water and 2% ELA HCl | | | <10 (>99.999% kill reduction) |
| 5% Mastic water | | 3.1 × 10$^4$ (<99% kill reduction) | |
| 1% Sodium p-anisate | | 2.3 × 10$^4$ (<99% kill reduction) | |
| 2% Mastic water and 0.5% sodium p-anisate | | 3.0 × 10$^3$ (>99.9% kill reduction) | |
| 25% Mastic water | 6.8 × 10$^4$ (<90% kill reduction) | | |
| 2.5% Quinic acid | 1.4 × 10$^5$ (<90% kill reduction) | | |
| 4% Mastic water and 1% Quinic acid | 6.9 × 10$^2$ (>99.9% kill reduction) | | |

From the table, synergism for the combinations above against mixed bacteria in shampoo was calculated by the method described in C. E. Kull et al., "Mixtures of Quaternary Ammonium Compounds and Long-chain Fatty Acids as Antifungal Agents", Applied Microbiology, 9:538-541 (1961). The synergism value $(Q_A/Q_a+Q_B/Q_b)$ was determined. $Q_A$ and $Q_B$ are concentrations of the first and second components, respectively, (in percent by weight) in the mixture, which yielded 100% retardation of the bacteria. $Q_a$ is the concentration of the first component alone (in percent by weight) required to yield 100% retardation of the bacteria. $Q_b$ is the concentration of the second component alone (in percent by weight) required to yield 100% retardation of the bacteria. When the value of $(Q_A/Q_a+Q_B/Q_b)$ is less than one, the mixture is synergistic. Values for $(Q_A/Q_a+Q_B/Q_b)$ of 1 and greater represent an additive effect and an antagonistic effect, respectively. Here, $(Q_A/Q_a+Q_B/Q_b)$ is ((0.2%/>0.5%)+(0.05%/>0.1%)) or <0.9. Accordingly, the mixture of 0.2% mastic oil and 0.05% piroctine olamine is synergistic. The mixture of 2% mastic water and 2% ELA, the mixture of 2% mastic water and 0.5% sodium p-anisate, and the mixture of 4% mastic water and 1% quinic acid are also synergistic.

All references, patent applications, and patents cited herein are hereby incorporated by reference.

The invention claimed is:

1. A product comprising an effective amount to inhibit microbial growth in the product of (a) about 0.05 to about 0.5 wt. % mastic oil derived from *Pistacia lentiscus* and about 0.02 to about 0.08 wt. % piroctone olamine, (b) about 1.5 to about 2.5 wt. % mastic water derived from *Pistacia lentiscus* and about 1.5 to about 2.5 wt. % ethyl lauroyl arginate or a salt thereof, (c) about 1.5 to about 2.5 wt. % mastic water derived from *Pistacia lentiscus* and about 0.3 to about 0.7 wt. % p-anisic acid or a salt thereof, or (d) about 1 to about 4 wt. % mastic water derived from *Pistacia lentiscus* and about 1 to about 3 wt. % quinic acid, wherein the product is not intended for oral administration to an animal.

2. The product of claim 1, wherein the product comprises mastic oil derived from *Pistacia lentiscus* and piroctone olamine.

3. The product of claim 1, wherein the product comprises mastic water derived from *Pistacia lentiscus* and ethyl lauroyl arginate or a salt thereof.

4. The product of claim 1, wherein the product comprises mastic water derived from *Pistacia lentiscus* and ethyl lauroyl arginate HCl.

5. The product of claim 1, wherein the product comprises mastic water derived from *Pistacia lentiscus* and p-anisic acid or a salt thereof.

6. The product of claim 5, where the product comprises mastic water derived from *Pistacia lentiscus* and sodium p-anisate.

7. The product of claim 1, wherein the product comprises mastic water derived from *Pistacia lentiscus* and quinic acid.

8. The product of claim 1, wherein (i) the mastic water is soluble in water, (ii) the mastic water or mastic oil is naturally derived, (iii) the product is substantially free or free of artificial preservatives, (iv) the product is substantially free or free of parabens, or (v) any combination of any of the foregoing.

9. The product of claim 1, wherein the product is a household, industrial, or institutional product.

10. The product of claim 1, wherein the product is a personal care product.

11. The product of claim 10, wherein the personal care product is a shampoo, body lotion, conditioner, or soap.

12. The product of claim 1, wherein the product is substantially free of isothiazolinones.

13. The product of claim 12, wherein the product comprises ethyl lauroyl arginate HCl.

14. The product of claim 12, where the product comprises sodium p-anisate.

15. The product of claim 12, where the product comprises quinic acid.

16. The product of claim 1, comprising an effective amount to inhibit microbial growth in the product of (a) about 0.2 wt. % mastic oil derived from *Pistacia lentiscus* and about 0.05 wt. % piroctone olamine, (b) about 2 wt. % mastic water derived from *Pistacia lentiscus* and about 2 wt. % ethyl lauroyl arginate or a salt thereof, (c) about 2 wt. % mastic water derived from *Pistacia lentiscus* and about 0.5 wt. % p-anisic acid or a salt thereof, or (d) about 4 wt. % mastic water derived from *Pistacia lentiscus* and about 1 wt. % quinic acid, wherein the product is not intended for oral administration to an animal.

* * * * *